(12) United States Patent
Park et al.

(10) Patent No.: US 8,990,231 B2
(45) Date of Patent: Mar. 24, 2015

(54) COOPERATION-BASED METHOD OF MANAGING, DISPLAYING, AND UPDATING DNA SEQUENCE DATA

(75) Inventors: Minseo Park, Seoul (KR); Jung-Youn Lee, Seoul (KR)

(73) Assignee: Samsung SDS Co., Ltd., Seoul (KR)

( * ) Notice: Subject to any disclaimer, the term of this patent is extended or adjusted under 35 U.S.C. 154(b) by 34 days.

(21) Appl. No.: 13/283,899

(22) Filed: Oct. 28, 2011

(65) Prior Publication Data

US 2012/0110430 A1    May 3, 2012

(30) Foreign Application Priority Data

Oct. 28, 2010  (KR) .......................... 10-2010-0106124

(51) Int. Cl.
G06F 7/00 (2006.01)
G06F 17/30 (2006.01)
G06F 19/26 (2011.01)
G06F 19/28 (2011.01)
G06F 19/18 (2011.01)

(52) U.S. Cl.
CPC ................ G06F 19/26 (2013.01); G06F 19/18 (2013.01); G06F 19/28 (2013.01)
USPC .............................. 707/758; 707/749; 345/6

(58) Field of Classification Search
None
See application file for complete search history.

(56) References Cited

U.S. PATENT DOCUMENTS

| | | | |
|---|---|---|---|
| 5,717,922 A * | 2/1998 | Hohensee et al. ................ 1/1 |
| 5,912,126 A * | 6/1999 | Darzynkiewicz et al. ... 435/6.12 |
| 6,027,625 A * | 2/2000 | Stein et al. .................. 204/466 |
| 6,687,878 B1 * | 2/2004 | Eintracht et al. .............. 715/201 |
| 6,775,622 B1 * | 8/2004 | Holloway ....................... 702/20 |
| 6,941,317 B1 * | 9/2005 | Chamberlin et al. ........ 435/6.12 |
| 2002/0168664 A1 * | 11/2002 | Murray et al. ..................... 435/6 |
| 2002/0169564 A1 * | 11/2002 | Delaney et al. ................. 702/20 |
| 2002/0187480 A1 * | 12/2002 | Brandon ............................ 435/6 |
| 2003/0187587 A1 * | 10/2003 | Swindells et al. .............. 702/19 |

(Continued)

FOREIGN PATENT DOCUMENTS

| | | |
|---|---|---|
| EP | 1067466 A2 * | 1/2001 |
| EP | 1 300 778 A1 | 4/2003 |

(Continued)

OTHER PUBLICATIONS

The UCSC genome browser database: update 2006, Hinrichs et al, Nucleic Acids Research, 34, pp. D590-D598, 2006.*

(Continued)

*Primary Examiner* — Augustine K Obisesan
(74) *Attorney, Agent, or Firm* — Sughrue Mion, PLLC (57) ABSTRACT

A cooperation-based method and system of managing, displaying, and updating DNA sequence data including receiving annotation data inputted by a user for an anchor corresponding to at least one base of a DNA sequence, and storing the received annotation data in an annotation data table which includes one or more columns for annotation data; receiving data about a position of an anchor which corresponds to at least one base of a DNA sequence in the DNA sequence, and displaying the position of the anchor on a DNA sequence map based on the received data; and getting input of a position at which an annotation is to be input on a DNA sequence map, displaying an annotation input interface which includes an edit region for inputting an annotation, and transmitting annotation data including annotation contents inputted through the edit region and the inputted position to a DNA sequence data storage device.

12 Claims, 5 Drawing Sheets

(56) References Cited

U.S. PATENT DOCUMENTS

| | | | |
|---|---|---|---|
| 2003/0200034 A1* | 10/2003 | Fellenberg et al. | 702/20 |
| 2003/0220820 A1* | 11/2003 | Sears et al. | 705/3 |
| 2004/0012633 A1* | 1/2004 | Helt | 345/764 |
| 2004/0101903 A1* | 5/2004 | Rigoutsos | 435/7.1 |
| 2004/0171051 A1* | 9/2004 | Holloway | 435/6 |
| 2004/0241730 A1* | 12/2004 | Yakhini et al. | 435/6 |
| 2005/0010373 A1* | 1/2005 | Varpela et al. | 702/20 |
| 2005/0049795 A1* | 3/2005 | Fikuda et al. | 702/20 |
| 2005/0187717 A1* | 8/2005 | Paxson et al. | 702/19 |
| 2006/0085138 A1* | 4/2006 | Klingenhoff | 702/20 |
| 2006/0150079 A1* | 7/2006 | Albornoz et al. | 715/512 |
| 2006/0210972 A1* | 9/2006 | Arthur et al. | 435/6 |
| 2007/0005592 A1* | 1/2007 | Kender et al. | 707/6 |
| 2007/0021919 A1* | 1/2007 | Leproust et al. | 702/19 |
| 2007/0255512 A1* | 11/2007 | Delenstarr et al. | 702/35 |
| 2007/0294614 A1* | 12/2007 | Jacquin et al. | 715/512 |
| 2008/0085284 A1* | 4/2008 | Patell et al. | 424/184.1 |
| 2009/0183268 A1* | 7/2009 | Kingsmore | 800/9 |
| 2009/0240441 A1* | 9/2009 | Lapidus | 702/20 |
| 2010/0049704 A1* | 2/2010 | Sumiya | 707/5 |
| 2010/0262659 A1* | 10/2010 | Christiansen et al. | 709/205 |
| 2011/0047189 A1* | 2/2011 | Will et al. | 707/803 |
| 2011/0059853 A1* | 3/2011 | Emler et al. | 506/8 |
| 2011/0281273 A1* | 11/2011 | Sugahara et al. | 435/6.12 |

FOREIGN PATENT DOCUMENTS

| | | |
|---|---|---|
| JP | 5225194 A | 9/1993 |
| JP | 2000105731 A | 4/2000 |
| JP | 2003526133 A | 9/2003 |
| JP | 200587160 A | 4/2005 |
| JP | 200897320 A | 4/2008 |
| JP | 2010-72827 A | 4/2010 |
| KR | 10-2010-0077895 A | 7/2010 |
| WO | WO 2004034277 A1 * | 4/2004 |
| WO | WO 2005071058 A2 * | 8/2005 |
| WO | WO 2008129459 A2 * | 10/2008 |
| WO | WO 2009046021 A1 * | 4/2009 |
| WO | WO 2009130520 A1 * | 10/2009 |

OTHER PUBLICATIONS

Communication issued on Feb. 10, 2012 by the Korea Intellectual Property Office in the counterpart Korean Patent Application No. 10-2010-0106124.

Stein, L. D. et. al. "The Generic Genome Browser: A Building Block for a Model Organism System Database", Genome Research, Dec. 2002, pp. 1599-1610.

Communication, dated Sep. 6, 2013, issued by the Japanese Patent Office in counterpart Japanese Application No. 2011-235331.

Fujita, Pauline A., et al, "The UCSC Genome Browser database: update 2011," Nucleic Acids Research, 2011, vol. 39, published online Oct. 18, 2010, pp. 1-8.

Communication, dated Apr. 25, 2014, issued by the Japanese Patent Office in counterpart Japanese Application No. 2011-235331.

Communication, dated Apr. 2, 2014, issued by the State Intellectual Property Office of the People's Republic of China in counterpart Chinese Application No. 201110342773.4.

Karolchik, et al.; "The UCSC Genome Browser", Current Protocols in Bioinformatics, Dec. 2009, 26 pages total.

Sherry, et al.; "dbSNP: the NCBI Database of Genetic Variation", Nucleic Acids Research, Jan. 2001, vol. 29, No. 1, 4 pages total.

D'Ascenzo, et al.; "PeerGAD: a Peer-Review-Based and Community-Centric Web Application for Viewing and Annotating Prokaryotic Genome Sequences", Nucleic Acids Research, Jun. 2004, vol. 32, No. 10, 12 pages total.

Huss, et al.; "A Gene Wiki for Community Annotation of Gene Function", PLoS Biology, Jul. 2008, vol. 6, No. 7, 6 pages total.

Donlin, "Using the Generic Genome Browser (GBrowse)", Current Protocols in Bioinformatics, Dec. 2009, 26 pages total.

Communication dated Jan. 19, 2015, issued by the European Patent Office in counterpart European Application No. 11186602.6.

* cited by examiner

| CHROMOSOME IDENTIFICATION INFORMATION | POSITION INFORMATION | AUTHOR | CREATION TIME | ANNOTATION TYPE | EVALUATION VALUE | ANNOTATION CONTENTS |
|---|---|---|---|---|---|---|
| | | | | | | |
| | | | | | | |
| | | | | | | |

FIG. 6

COOPERATION-BASED METHOD OF MANAGING, DISPLAYING, AND UPDATING DNA SEQUENCE DATA

This application claims priority from Korean Patent Application No. 10-2010-0106124 filed on Oct. 28, 2010 in the Korean Intellectual Property Office, the disclosure of which is incorporated herein by reference in its entirety.

BACKGROUND OF THE INVENTION

1. Field of the Invention

The present invention relates to a cooperation-based method of managing, displaying, and updating DNA sequence data, and more particularly, to a cooperation-based method of managing, displaying, and updating DNA sequence data, the method enabling researchers to cooperate with each other through annotations for one or more anchors corresponding to one or more bases contained in DNA sequence data.

2. Description of the Related Art

GBrowse is a genetic information browser utilized by many research institutes worldwide. Although GBrowse is based on a database called Mysgl™, it stores read data as file-based data. Since the volume of next-generation sequencing (NGS) data is far larger than that of general genetic information, existing genetic information browser such as GBrowse cannot be applied as it is to the NGS (Next Generation Sequencing) data. Therefore, attempts were made in 2009 to display the NGS data. As a result, we can display the NGS read data.

Integrative genomics viewer (IGV) is a browser developed to display DNA sequence data on a local computer. IGV is designed to include not only the NGS data to the input but also experimental data such as a microarray. In the case of the NGS data, data in a sequence alignment/map (SAM) or binary alignment/map (BAM) file format may be received as inputs. A user may install this tool in his or her computer, obtain a necessary file, and import the file to the tool.

Conventional genetic information browsers such as those described above can display a DNA sequence but cannot reflect a user' comments on the specific DNA sequence.

The gene research field requires vast knowledge. In particular, analyzing a gene through whole genome sequencing cannot be done by one person or researchers of one research institute. Most whole genome sequencing projects are carried out with the participation of many countries and research institutes, actually. In this case, an active exchange/interchange of academic research data is crucial. However, information about researchers' research results is available only in papers published by the researchers, and it requires a considerable amount of time and cost to collect and analyze these papers. Further, when papers are read and interpreted by professional researchers, research results are often not shared freely. On this wise since the current laboratory system is like a closed society, a system that can easily collect and spread research results is required.

SUMMARY OF THE INVENTION

Aspects of the present invention provide a cooperation-based method of managing, displaying, and updating DNA sequence data, the method allowing research results related to a DNA sequence to be shared freely.

Aspects of the present invention also provide a method of managing, displaying, and updating DNA sequence data, the method allowing a user to select desired annotations by filtering recorded annotation information and display the selected annotations.

Aspects of the present invention also provide a method of managing, displaying, and updating DNA sequence data, the method displaying the relationship between DNA sequence positions which are related to a certain disease or race.

However, aspects of the present invention are not restricted to the one set forth herein. The above and other aspects of the present invention will become more apparent to one of ordinary skill in the art to which the present invention pertains by referencing the detailed description of the present invention given below.

According to an aspect of the present invention, there is provided a cooperation-based method of managing DNA sequence data, the method comprising receiving annotation data inputted for an anchor corresponding to at least one base of a DNA sequence; and storing the received annotation data in an Annotation data table which comprises one or more columns for annotation data.

According to another aspect of the present invention, there is provided a cooperation-based method of displaying DNA sequence data, the method comprising: receiving data about a position of a anchor, which corresponds to at least one base of a DNA sequence, in the DNA sequence; and displaying the position of the anchor on a DNA sequence map based on the received data.

According to another aspect of the present invention, there is provided a cooperation-based method of updating DNA sequence data, the method comprising: getting input of a position, at which an annotation is to be input, on a DNA sequence map; displaying an annotation input interface which comprises an edit region for inputting an annotation; and transmitting annotation data comprising annotation contents inputted through the edit region and the inputted position to a DNA sequence data storage device.

According to another aspect of the present invention, there is provided a cooperation-based system for managing DNA sequence data, the system comprising: a database (DB) server storing annotation data for a anchor, wherein the anchor corresponds to at least one base of a DNA sequence, and DNA sequence data; and a service server transmitting a portion of the annotation data and a portion of the DNA sequence data corresponding to an area requested by a client, to the client, receiving annotation data for a anchor comprising position information of the anchor from the client, processing the received annotation data into an annotation data format, and storing the processed annotation data in the DB server.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE INVENTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. The same reference numbers indicate the same components throughout the specification. In the attached figures, the thickness of layers and regions is exaggerated for clarity.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

The configuration and operation of a cooperation-based system for displaying and updating a DNA sequence according to an embodiment of the present invention will hereinafter be described with reference to FIG. 1.

Figure 1:
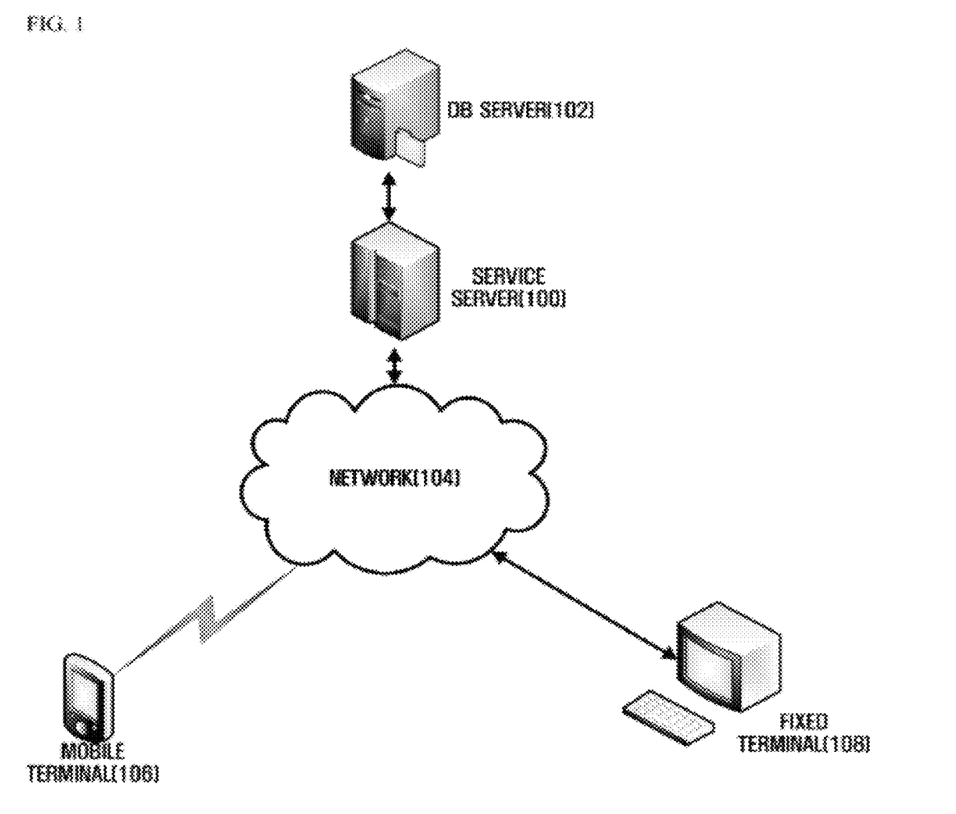
FIG. 1 is a schematic illustration of cooperation-based DNA sequence display and update system in an embodiment of this invention.

FIG. 1 is a diagram illustrating the configuration of a cooperation-based system for displaying and updating a DNA sequence according to an embodiment of the present invention. Referring to FIG. 1, the cooperation-based system for displaying and updating a DNA sequence according to the current embodiment of the present invention may include a service server 100, a database (DB) server 102, a fixed terminal 108, and a network 104. Optionally, the system may further include a mobile terminal 106. The network 104 connects the service server 100, the fixed terminal 108 and the mobile terminal 106. The network 104 can use any type of communication method and any connection technology. In the drawing, the DB server 102 is connected directly to the service server 100. However, the DB server 102 can also be connected to the service server 100 through the network 104. In addition, while the DB server 102 and the service server 100 are illustrated in the drawing as separate devices, they can also be integrated into one device.

The DB server 102 stores DNA sequence data and annotation data table. The DB server 102 may be, but is not limited to, at least one of a nonvolatile memory such as a cache, a read only memory (ROM), a programmable ROM (PROM), an erasable programmable ROM (EPROM), an electrically erasable programmable ROM (EEPROM) or a flash memory, a volatile memory such as a random access memory (RAM), and a storage medium such as a hard disk drive.

The DNA sequence data comprises information about bases constituting the DNA sequence. The base of DNA sequence, as it is already known in the art, means nucleotides (base) such as Adenine, Guanine, Cytosine and Thymine, which constitutes the DNA sequence.

The annotation data includes data on each input annotation for an anchor. For example, the annotation data may contain information about the author of an annotation, the creation time of the annotation, the type of the annotation, an evaluation value of the annotation calculated based on evaluations by users other than the author of the annotation, and annotation contents (i.e., data on the content of the annotation). Two or more annotations may be written for one anchor. Accordingly, two or more pieces of annotation data may exist for one anchor. The annotation data table can be interpreted as a database table comprising the annotation data.

Figure 5:
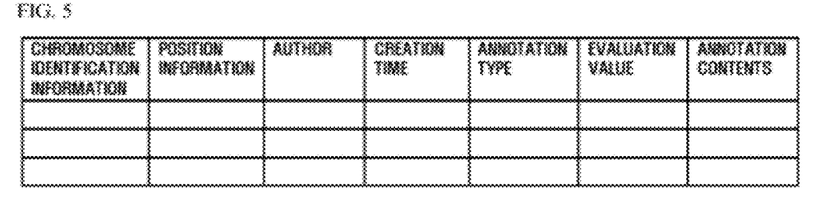
FIG. 5 shows an annotation data table in an embodiment of this invention.

FIG. 5 shows an example of the annotation data table according to the current embodiment of the present invention. Information about each annotation written for a specific position of a specific chromosome may be stored in the DB server 102. A row in the annotation data table in FIG. 5 comprises data of an annotation, and attributes of the annotation such as annotation author or annotation contents are inputted in each column of the annotation data table.

The DB server 102 can store the annotation data in a various data format, therefore data storing format of the annotation data is not limited to the annotation data table in FIG. 5.

The service server 100 may control the DB server 102 to store annotation data received from the mobile terminal 106 or the fixed terminal 108. For example, when the mobile terminal 106 or the fixed terminal 108 transmits inputted annotation data to the service server 100, the service server 100 receives the annotation data, generates annotation row data for storing the received annotation data and controls the DB server 102 to insert the received annotation data by providing the generated annotation row data to the DB server 102.

The columns for the annotation data may include an annotation type column that stores one of pre-designated annotation types. The pre-designated annotation types may include an 'experimental result memo' type, a 'reply' type to an existing annotation, and a 'correction/opinion' type about an existing annotation. In particular, an existing annotation may have an evaluation value calculated based on evaluations by users other than the author of the annotation. Thus, an annotation evaluation value column that stores the evaluation value may further be included in the columns for the annotation data.

As mentioned above, to manage keywords of annotations, the columns for the annotation data may include a contents column which stores a character string representing the content of an annotation and a keyword column which stores information about a keyword extracted from the character string by comparing the character string with a keyword dictionary.

Hereinafter, the operation of the cooperation-based system for displaying and updating a DNA sequence according to the current embodiment will be described with reference to FIG. 2.

Figure 2:
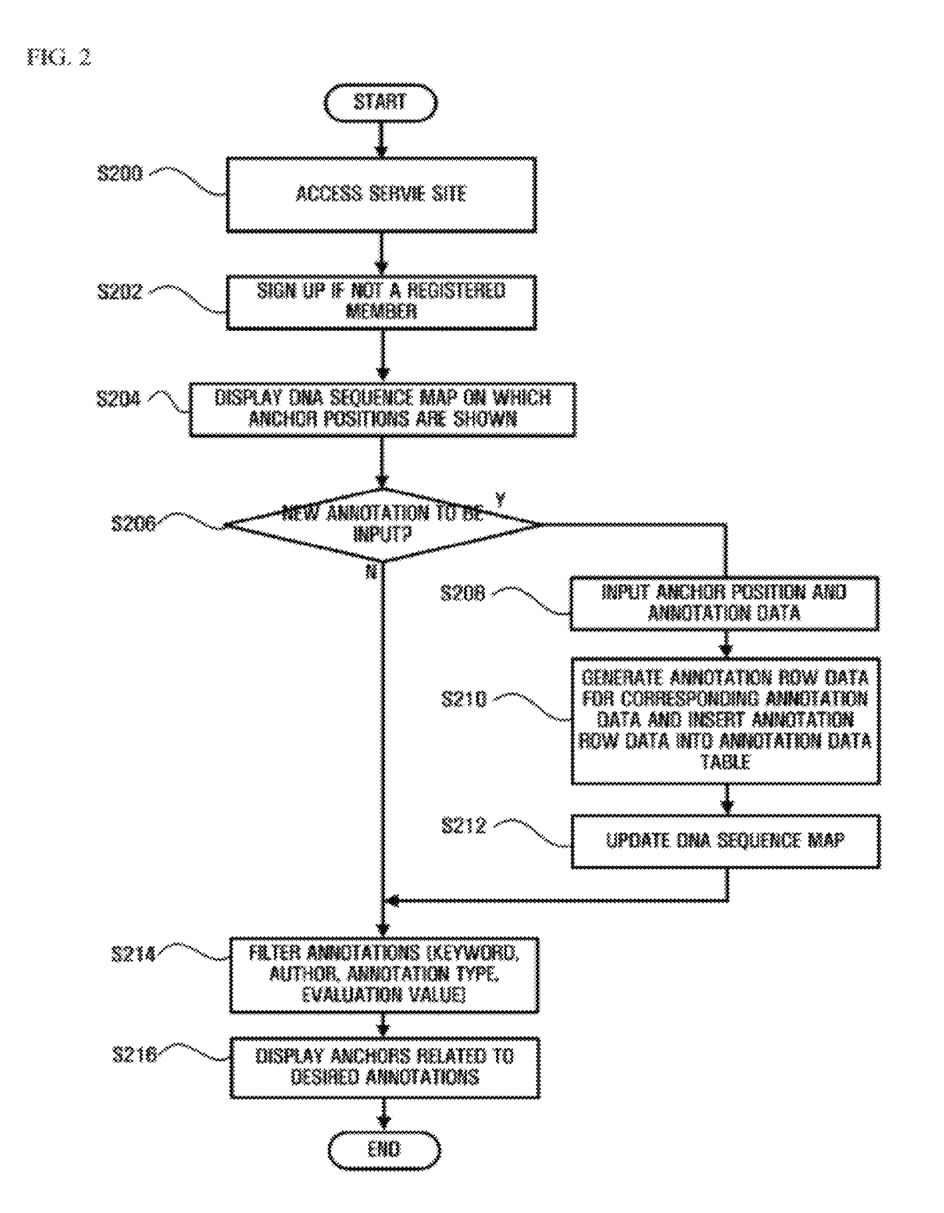
FIG. 2 shows a flowchart depicting the method of cooperation-based DNA sequence displaying and updating in an embodiment of this invention.

Referring to FIG. 2, a user accesses a service site for displaying and annotating DNA sequence using the mobile terminal 106 or the fixed terminal 108 (operation S200). The service site may be provided by the service server 100. That is, the service server 100 may have the function of a web server.

Next, the user logs into the service site. If the user is not a registered member of the service site, the user signs up for the service site (operation S202). In the sign-up process, the user may input information about his or her name, job and interests. The inputting of the job and interests may be done by selecting an item from a pre-input list of items. The information input during the sign-up process may be stored in the DB server 102.

Once the user logs in, a DNA sequence map showing the positions of anchors designated by the user or another individual is displayed (operation S204). If no anchors exist within the display range of the DNA sequence map, only the DNA sequence map, for example an image showing the arrangement of DNA sequence in a zoomed-out state, on a conventional gene browser.

Figure 3:
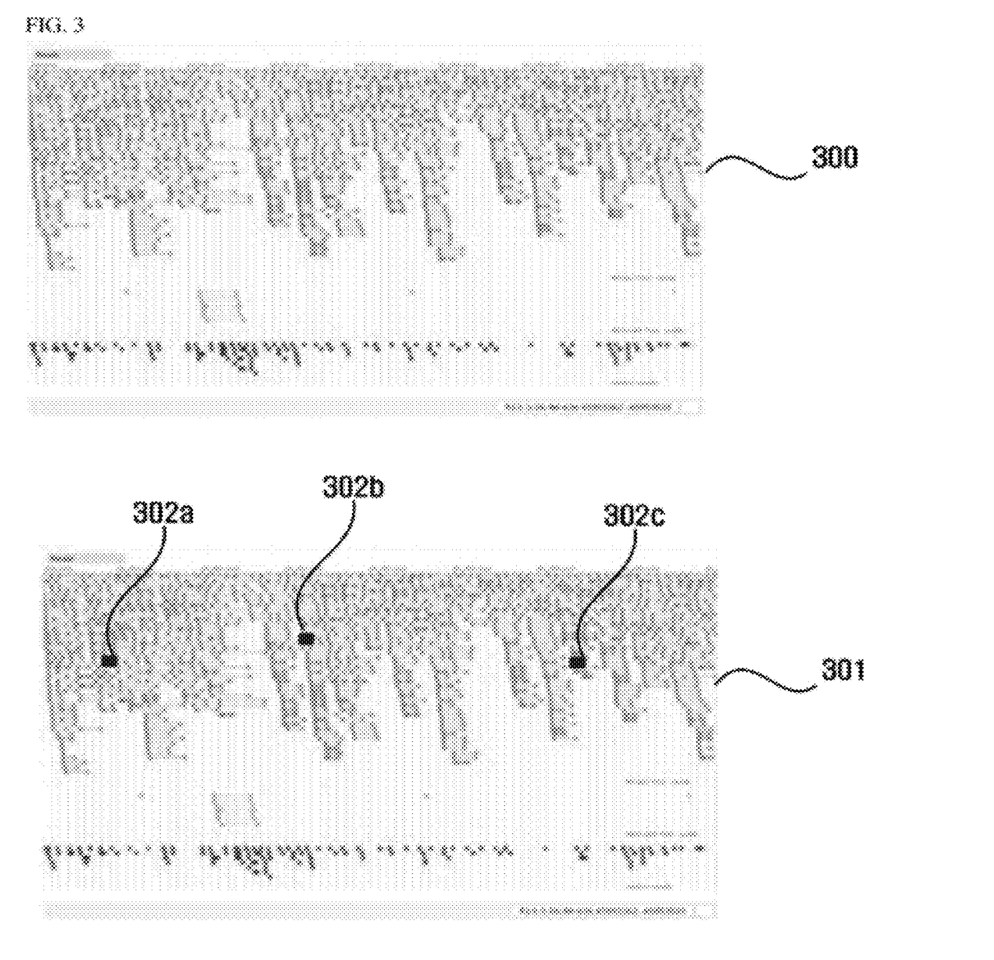
FIG. 3 depicts DNA map displayed in an embodiment of this invention.

In FIG. 3, a DNA sequence map 300 and a DNA sequence map 301 on which positions of anchors 302a through 302c are shown are illustrated. Depending on setting, when a user logs in, only anchors generated by the user or an individual designated by the user may be displayed or only anchors corresponding to annotations written by the user or an individual designated by the user may be displayed.

Anchors may be grouped according to their attributes, on a DNA sequence map. For example, anchors related to disease A may be displayed as a shape, or the relationship between these anchors may be marked on the DNA sequence map.

Figure 6:
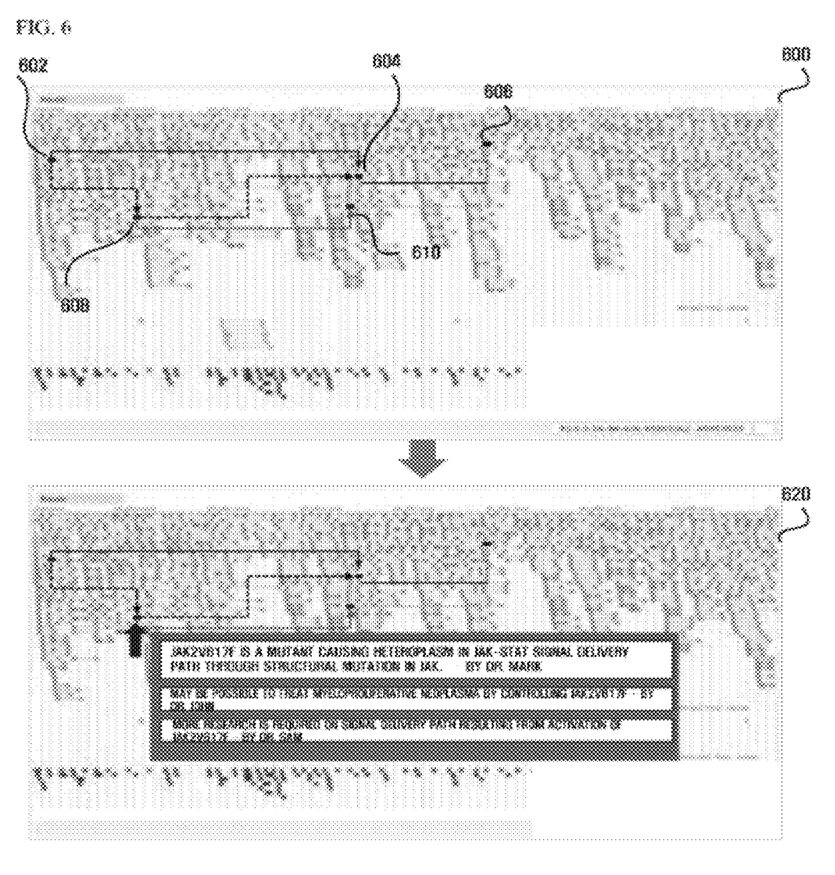
FIG. 6 depicts displaying grouped anchors in an embodiment of this invention.

FIG. 6 shows example groups of anchors displayed. Referring to FIG. 6, on a DNA sequence map 600, anchors 602, 604 and 606 related to leukemia are connected to each other by an arrow, and anchors 608 and 610 related to Jak2 Marker are connected to each other by an arrow. In addition, anchors 602, 608 and 604 related to a certain race are connected to each other by a dotted arrow.

The anchors may also be grouped based on a value entered in the keyword column. An anchor having at least one annotation whose stored keyword is leukemia or an anchor having more than a predetermined number of such annotations may be included in a group of leukemia-related anchors.

The anchors may also be grouped based on a keyword extracted from words stored in the annotation contents.

When intending to view annotations for an anchor, a user may select the anchor and view the annotations for the anchor. An interface through which a user is viewing annotations is shown on the DNA sequence map 620 of FIG. 6.

Only three annotations are shown on the DNA sequence map 620. However, an anchor which is being actively researched may have many annotations. When two or more annotations exist for a selected anchor, they may be arranged and displayed according to scores calculated based on the similarity between a job of a current user and that of an annotation author contained in annotation data, the similarity between interests of the current user and those of the annotation author contained in the annotation data, and an evaluation value of the annotation data. In this case, an annotation most suitable for the user may be displayed at the top.

Alternatively, a latest annotation may be displayed first. Alternatively, an annotation written by an individual having the same interests or job as the user may be displayed first based on user profiles. Alternatively, an annotation of a certain annotation type may be displayed first.

An annotation input interface displayed when the user to input a new annotation, will now be described with reference to FIG. 4.

To input a new annotation, the user enters a pre-designated annotation input command (operation S208). The annotation input command may be entered by selecting an item in a pop-up menu brought up by a right-button click on a mouse. That is, when intending to input an annotation for a pre-generated anchor, the user may place a cursor on the pre-generated anchor and enter the annotation input command. In addition, when intending to generate a new anchor and input an annotation for the generated anchor, the user may place the cursor on a position 401, at which the user desires to generate an anchor, in a DNA sequence and enter the annotation input command.

Figure 4:
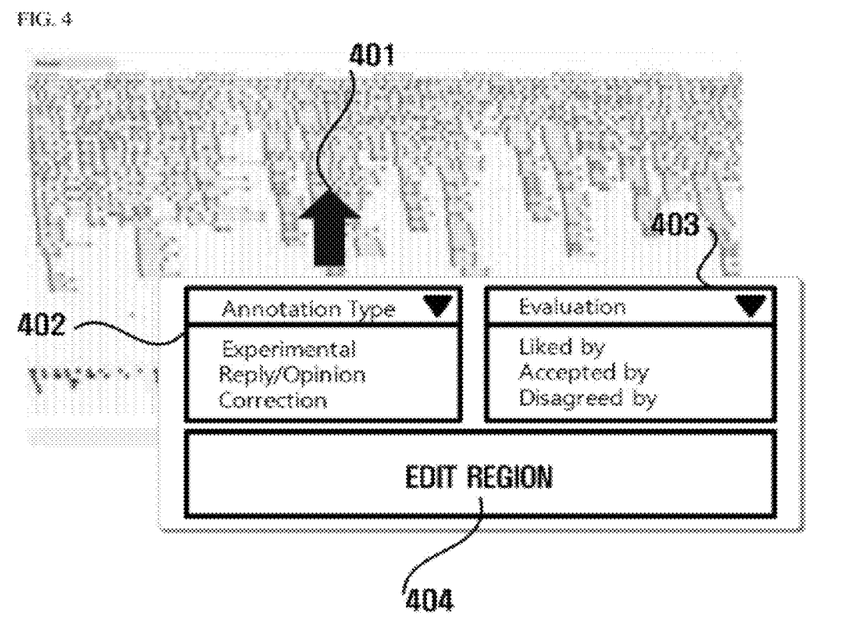
FIG. 4 is a schematic illustration of an annotation input interface displayed when the user tries to input a new annotation in an embodiment of this invention.

When the annotation input command is entered, the annotation input interface as shown in FIG. 4 may be displayed.

The annotation input interface may include an annotation type input region 402, an evaluation value input region 403, and an edit region 404.

The annotation type input region 402 may be constructed as a user interface through which one of predetermined annotation types can be selected. When an annotation is to be input as a reply to an existing annotation, the evaluation value input region 403 may be used to input evaluation values for the evaluation of the existing annotation. The edit region 404 may be constructed as an edit control in which a character string can be entered.

A region (not shown) for designating whether to make inputted annotations public may also be included in the annotation input interface. The inputted annotations may all be made public or private by a subscriber's configuration. Further, a certain type of annotations may be designated as public. Further, when a device used to access the service site is the mobile terminal 106, all input annotations may be designated as private. Annotations designated as private can be viewed only by their authors.

Data input by the user through the annotation input interface is transmitted to the service server 100. The service server 100 receives the data, generates annotation row data to be stored in the Annotation data table, and provides the annotation row data to the DB server 102 so that the annotation row data is inserted into the Annotation data table (operation S210).

The service server 100 transmits data to the fixed terminal 108 or the mobile terminal 106 so as to allow the fixed terminal 108 or the mobile terminal 106 to update the DNA sequence map by reflecting the result of inputting a new annotation or anchor. The fixed terminal 108 or the mobile terminal 106 receives the data, updates the DNA sequence map, and displays the updated DNA sequence map.

The user may input a search condition for annotations, so that annotations that meet the search condition and anchors related to the annotations can be displayed (operation S214). Here, a keyword, an author, an annotation type, and an evaluation may be used as the search condition. In addition, the anchors related to the annotations that meet the search condition are displayed (operation S216).

According to the present invention, a DNA sequence browsing method which supports cooperation between researchers can be provided. The method allows the researchers to freely share their research into DNA sequences.

Recorded annotation information can be filtered to display only annotations desired by a user.

In addition, the relationship between positions, which are related to a certain disease or race, in a DNA sequence, can be marked.

In concluding the detailed description, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation.

What is claimed is:

1. A cooperation-based method of managing DNA sequence data, the method comprising:
   receiving annotation data inputted by a user for an anchor corresponding to at least one base of a DNA sequence;
   storing the received annotation data in an annotation data table which comprises one or more columns for annotation data; and displaying annotation contents contained in the annotation data for the anchor corresponding to the at least one base of the DNA sequence, wherein the anchor corresponding to the at least one base of the DNA sequence is displayed on a DNA sequence map, wherein the received annotation data inputted by the user for the anchor corresponding to the at least one base of the DNA sequence comprises at least one of an experimental results memo, a reply to an existing annotation, or a correction/opinion regarding an existing annotation, wherein the columns for the annotation data comprise a contents column which stores a character string representing the content of an annotation and at least one of an annotation type column which stores one of pre-designated annotation types, an annotation evaluation value column which stores an evaluation value calculated based on evaluations by users other than an annotation author, or a keyword column which stores information about a keyword extracted from the character string by comparing the character string with a keyword dictionary, and wherein the displaying of the annotation contents contained in the annotation data for the anchor comprises, when two or more annotations exist for the anchor, arranging and displaying the annotations according to scores calculated based on a similarity between a job of the user and that of an annotation author contained in the annotation data, the similarity between interests of the user and those of the annotation author contained in the annotation data, and an evaluation value of the annotation data.

2. A cooperation-based method of displaying DNA sequence data, the method comprising:
  receiving data about a position of each of at least one anchor, which corresponds to at least one base of a DNA sequence, in the DNA sequence;
  displaying the position of each of the at least one anchor on a DNA sequence map based on the received data;
  receiving annotation data for the at least one anchor;
  receiving information about one or more selected anchors; and
  displaying annotation contents contained in annotation data for the one or more selected anchors on the DNA sequence map,
  wherein the annotation contents comprise at least one of an experimental results memo, a reply to an existing annotation, or a correction/opinion regarding an existing annotation,
  wherein the displaying of the annotation contents contained in the annotation data for the one or more selected anchors comprises, when two or more annotations exist for each of the one or more selected anchors, arranging and displaying the annotations according to scores calculated based on the similarity between a job of a current user and that of an annotation author contained in the annotation data, the similarity between interests of the current user and those of the annotation author contained in the annotation data, and an evaluation value of the annotation data.

3. The cooperation-based method of claim 2, further comprising:
  grouping the at least one anchor based on a keyword included in annotation contents contained in the annotation data and displaying the grouped anchors on the DNA sequence map.

4. The cooperation-based method of claim 2,
  wherein the annotation data comprises author information, annotation type information, evaluation value information, and the annotation contents; and
  further comprising filtering the annotation data based on at least one of the author information, the annotation type information, the evaluation value information, or the annotation contents and displaying the filtered annotation data.

5. The cooperation-based method of claim 4, wherein the filtering of the annotation data and the displaying of the filtered data comprises filtering the annotation data using values calculated based on the similarity between a job of a current user and that of an annotation author contained in the annotation data and the similarity between interests of the current user and those of the annotation author contained in the annotation data and displaying the filtered annotation data.

6. A cooperation-based method of updating DNA sequence data, the method comprising:
  getting input of a position, at which an annotation is to be input, on a DNA sequence map, the position corresponding to at least one base on the DNA sequence map;
  displaying an annotation input interface which comprises an edit region for inputting an annotation;
  transmitting annotation data comprising annotation contents inputted through the edit region and the inputted position to a DNA sequence data storage device; and
  displaying the annotation contents contained in the annotation data for the position corresponding to the at least one base on the DNA sequence map,
  wherein the annotation contents inputted through the edit region correspond to the at least one base on the DNA sequence map and comprise at least one of an experimental results memo, a reply to an existing annotation, or a correction/opinion regarding an existing annotation, and
  wherein the displaying of the annotation contents contained in the annotation data for the position comprises, when two or more annotations exist for the position, arranging and displaying the annotations according to scores calculated based on a similarity between a job of a current user and that of an annotation author contained in the annotation data, the similarity between interests of the current user and those of the annotation author contained in the annotation data, and an evaluation value of the annotation data.

7. The cooperation-based method of claim 6, wherein the displaying the annotation input interface comprises displaying the annotation input interface which further comprises an annotation type selection region, and the transmitting annotation data storage device comprises transmitting annotation data, which further comprise an annotation type selected through the annotation type selection region, to the DNA sequence data storage device.

8. The cooperation-based method of claim 7, wherein the getting input of a position comprises getting input of a position of one of anchors shown on the DNA sequence map, the displaying of the annotation input interface comprises displaying the annotation input interface which further comprises an evaluation selection region for selecting an evaluation of an existing annotation when the selected annotation type is a reply type to the existing annotation, and the transmitting annotation data comprises transmitting information about the evaluation of the existing annotation selected through the evaluation selection region to the DNA sequence data storage device.

9. The cooperation-based method of claim 6, further comprising getting input for designating whether to make the inputted annotation contents public.

10. A cooperation-based system for managing DNA sequence data, the system comprising:
   a database (DB) server storing annotation data for an anchor, wherein the anchor corresponds to at least one base of a DNA sequence, and DNA sequence data; and
   a service server transmitting a portion of the annotation data and a portion of the DNA sequence data corresponding to an area requested by a client, to the client, receiving annotation data for an anchor comprising position information of the anchor from the client, processing the received annotation data into an annotation data format, and storing the processed annotation data in the DB server,
   wherein the received annotation data corresponds to the at least one base of the DNA sequence and comprises at least one of an experimental results memo, a reply to an existing annotation, or a correction/opinion regarding an existing annotation,
   wherein the annotation data comprise a contents which stores a character string representing the content of an annotation, and at least one of an annotation type which stores one of pre-designated annotation types, an annotation evaluation value which stores an evaluation value calculated based on evaluations by users other than an annotation author, or a keyword which stores information about a keyword extracted from the character string by comparing the character string with a keyword dictionary, and
   wherein the service server, in the transmitting the portion of the annotation data and the portion of the DNA sequence data corresponding to the area requested by the client, when two or more annotations exist for the anchor, arranges the annotations for display according to scores calculated based on a similarity between a job of a current user and that of an annotation author contained in the annotation data, the similarity between interests of the current user and those of the annotation author contained in the annotation data, and an evaluation value of the annotation data.

11. The cooperation-based system of claim 10, further comprising the client receiving the portion of the annotation data and the portion of the DNA sequence data from the service server, displaying a DNA sequence map on which position of the anchor contained in the portion of the annotation data are shown, getting input of position information of an anchor and annotation contents for the anchor from a user, and transmitting the inputted position information and annotation contents to the service server.

12. The cooperation-based system of claim 11, wherein the client groups the anchors based on a keyword included in annotation contents contained in the portion of the annotation data and displays the grouped anchors on the DNA sequence map.

* * * * *